United States Patent [19]

Meilland

[11] Patent Number: Plant 5,844

[45] Date of Patent: Dec. 30, 1986

[54] ROSE PLANT—MEIFULA VARIETY

[75] Inventor: Marie-Louise Meilland, Antibes, France

[73] Assignee: The Conard-Pyle Company, West Grove, Pa.

[21] Appl. No.: 659,838

[22] Filed: Oct. 11, 1984

[30] Foreign Application Priority Data

Oct. 12, 1983 [FR] France ..... 4209

[51] Int. Cl.[4] ..... A01H 5/00

[52] U.S. Cl. ..... Plt./20

[58] Field of Search ..... Plt./20–21

*Primary Examiner*—R. E. Bagwill

*Attorney, Agent, or Firm*—Burns, Doane, Swecker & Mathis

[57] ABSTRACT

A new and distinct variety of Hybrid Tea rose plant is provided which forms large, elegant very double blossoms which are of a velvet red coloration on the upper surface and of a cardinal red coloration on the under surface. The new variety is well adapted for the production of long-lasting cut flowers while being grown under greenhouse conditions. Such flowers are highly attractive and are produced on long stems.

6 Drawing Figures

SUMMARY OF THE INVENTION

The new variety of Hybrid Tea rose plant of the present invention was created by artificial pollination wherein two parents were crossed which previously had been studied in the hope that they would contribute the desired characteristics. The seed parent of the new variety was created by first crossing the Cancan variety (U.S. Plant Pat. No. 2,902) with an unnamed seedling to produce a parent which was crossed with an unnamed seedling. The pollen parent of the new variety was the product of the pollination of the Meger variety (non-patented) and the Karl Herbst variety (non-patented). The parentage of the new variety can be summarized as follows:

[(Unnamed Seedling × CANCAN) × Unnamed Seedling]
×
(MEGER × KARL HERBST).

The seeds resulting from the above pollination were sown and 72 plantlets were obtained which were physically and biologically different from each other. Selective study resulted in the identification of a single plant of the new variety. The desirable qualities of the new variety have been confirmed through extensive testing, and the importance of the new variety has been firmly established.

It was found that the new variety of Hybrid Tea rose plant of the present invention possesses the following combination of characteristics:

(a) from a physical point of view, the plant has medium green adult wood, an upright growth habit, and forms on long stems large, elegant very double blossoms of long duration which are of a velvet red coloration on the upper surface and of a cardinal red coloration on the under surface; and (b) from a biological point of view, the plant has vigorous vegetation, and exhibits good disease resistance.

The new variety meets the needs of the horticultural industry for all usages. It has been found, however, that the new variety particularly is well suited for being grown in greenhouses to produce quality cut flowers.

The blossoms of the new variety have been found to be long-lasting, and the petals detach cleanly.

The new variety has been found to undergo asexual propagation by a number of routes, including budding and grafting. The characteristics of the new variety have been found to be strictly transmissible by such asexual propagation from one generation to another.

The new variety has been named the Meifula variety.

BRIEF DESCRIPTION OF THE PHOTOGRAPH

The accompanying photograph shows as nearly true as it is reasonably possible to make the same in a color illustration of this character, typical specimens of plant parts of the new variety. The rose plants of the new variety described herein were grown at Cap d'Antibes, France, in a greenhouse.

FIG. 1 illustrates a specimen of a young shoot;

FIG. 2 illustrates a specimen of a flowering bud before the opening of the sepals;

FIG. 3 illustrates a specimen of a flowering bud at the opening of the sepals;

FIG. 4 illustrates a specimen of a flowering bud at the opening of the petals;

FIG. 5 illustrates a specimen of a flower at the beginning of the opening;

FIG. 7 illustrates a specimen of a fully open flower — plan view — reverse;

FIG. 10 illustrates a specimen of a floral receptacle showing the arrangement of the stamens and pistils;

FIG. 11 illustrates a specimen of a floral receptacle showing the arrangement of the pistils (stamens removed);

FIG. 13 illustrates a specimen of a main branch;

FIG. 14 illustrates a specimen of a leaf with three leaflets — upper surface;

FIG. 15 illustrates a specimen of a leaf with five leaflets — under surface; and FIG. 16 illustrates a specimen of a leaf with seven leaflets — upper surface.

DETAILED DESCRIPTION

Figures 6, 8, 9, 12:
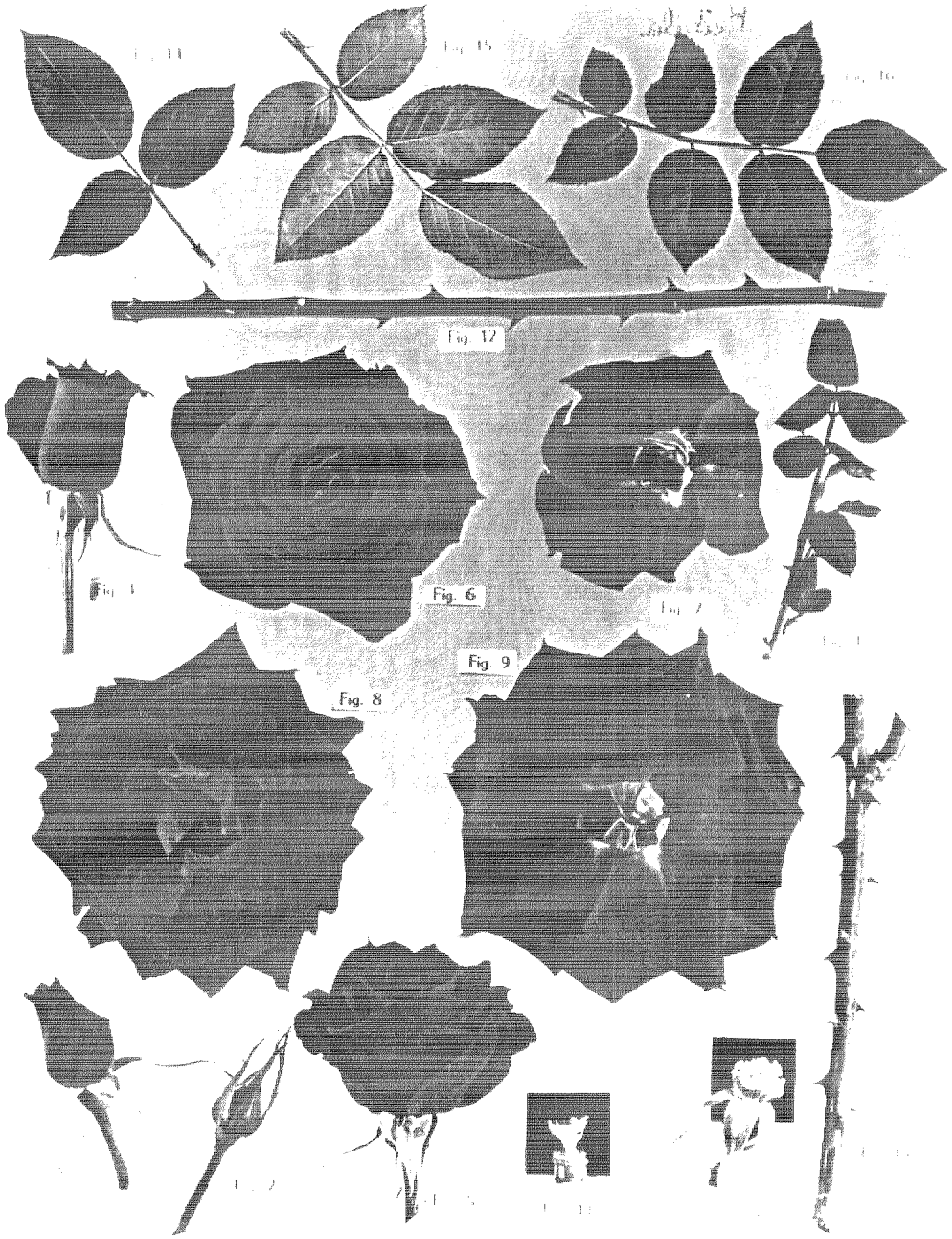
FIG. 6 illustrates a specimen of a fully open flower — plan view — obverse.
FIG. 8 illustrates a specimen of a fully open flower immediately prior to petal drop — plan view — obverse.
FIG. 9 illustrates a specimen of a fully open flower immediately prior to petal drop — plan view — reverse.
FIG. 12 illustrates a specimen of a young flowering stem.

The chart used in the identification of the colors is that of The Royal Horticultural Society (R.H.S. Colour Chart). The terminology preceding the numbered references has been added to designate in common terms the corresponding colors. The rose plants of the new variety described herein were grown at Cap d'Antibes, France, in a greenhouse.

Class: Hybrid Tea.

Plant:

*Height.*—When plants are pruned to 85 cm., flower bearing stems of approximately 50 to 120 cm. in length are produced.

*Habit.*—Upright.

Branches:

*Color.*—Young stems: light green, Yellow-Green Group 146C, more or less spotted with a reddish-brown tinge. Mature wood: medium green, Yellow-Green Group 146B.

*Thorns.*—Shape: Upper edge: straight with a slight curve. Lower edge: concave. Size: medium. Quantity: medium on young stems, fairly numerous on mature wood. Color: On young stems: reddish. On mature wood: greenish-red blended with havana brown coloration.

Leaves:

Stipules.—Large and linear.

*Petioles.*—Inner surface: grooved and reddish-brown on young foliage and medium green on adult foliage with somewhat glandular edges. Outer surface: light green and smooth.

*Leaflets.*—Number: 3, 5, and 7 (most often). Shape: elliptic and lanceolate at the base, sometimes asymmetrical, the margins tend to recurve toward the undersides. Serration: simple and regular. Texture: fairly consistent. General appearance: ample and brilliant foliage. Color (young foliage): Upper surface: Yellow-Green Group 144A shaded with a reddish tinge. Under surface: Yellow-Green Group 144A shaded with a reddish tinge. Color (adult foliage): Upper surface: dark green, Yellow-Green Group 147A. Under surface: medium green, Yellow-Green Group 147B, somewhat shaded with reddish coloration.

Inflorescence:

*Number of flowers.*—General one per stem.

*Peduncle.*—Straight, rigid, sometimes having small hairy thorns; its length is approximately 12 cm. on average.

*Sepals.*—Upper surface: tomentose, greenish in coloration. Under surface: clear green in coloration with a point which is more or less reddish and glandular, often bearing appendages on the edges.

*Buds.*—Shape: oblong. Length: approximately 3 cm. on average (not including the calyx). Size: rather thick. Color (when opening): Upper surface: dark velvet red (Red Group 45B). Under surface: dark cardinal red (slightly darker than Red Group 44A), more or less spotted with black coloration.

*Flower.*—Form: very double, the sides initially are substantially parallel, and subsequently open to the classic rose form. Diameter: approximately 12 to 13 cm. on average. Color (when opening begins): Upper surface: velvet red (Red Group 45B) and slightly lighter than the bud stage. Under surface: cardinal red (slightly darker than Red Group 44A). Color (when partially open): Upper surface: velvet red (slightly darker than Red Group 44A). Under surface: light cardinal red (Red Group 44A). Color (at end of opening): Upper surface: velvet red (slightly darker than Red Group 44B). Under surface: light cardinal red (Red group 44B). Fragrance: slight. Lasting quality: long. Corolla (petals): Form: generally round although sometimes have a small point at the tip of the petals; often one or two exterior petals have a large central greenish stripe. Number: approximately 43 on average. Detachment: the petals detach cleanly. Stamens: Number: approximately 174 on average. Anthers: color is typical for the genus. Pistils: Number: approximately 150 on average. Receptacle: light green in coloration, at the dehiscence of the anthers in longitudinal cross-section it is in the shape of a jug.

Development:

*Vegetation.*—Vigorous.

*Blossoming.*—Average.

*Aptitude to greenhouse forcing.*—Light.

*Disease resistence.*—Good.

I claim:

1. A new and distinct variety of Hybrid Tea rose plant characterized by the fact that:

(a) from a physical point of view, the plant has medium green adult wood, an upright growth habit, and forms on long stems large, elegant very double blossoms of long duration which are of a velvet red coloration on the upper surface and of a cardinal red coloration on the under surface; and (b) from a biological point of view, the plant has vigorous vegetation, and exhibits good disease resistance;

substantially as herein shown and described.

* * * * *